US008216587B1

(12) United States Patent
Berg et al.

(10) Patent No.: US 8,216,587 B1
(45) Date of Patent: Jul. 10, 2012

(54) METHOD OF VACCINATION

(75) Inventors: Kristian Berg, Heggedal (NO); Torunn E. Tjelle, Oslo (NO); Anders Høgset, Oslo (NO); Lina Prasmickaite, Oslo (NO)

(73) Assignee: PCI Biotech AS (NO)

(*) Notice: Subject to any disclaimer, the term of this patent is extended or adjusted under 35 U.S.C. 154(b) by 0 days.

(21) Appl. No.: 09/524,454

(22) Filed: Mar. 10, 2000

(30) Foreign Application Priority Data

Mar. 15, 1999 (GB) .................................. 9905911.5

(51) Int. Cl.
 A61K 39/00 (2006.01)
 A61K 39/38 (2006.01)
 A61K 39/385 (2006.01)
(52) U.S. Cl. .................................. 424/193.1; 424/184.1
(58) Field of Classification Search ............... 424/278.1, 424/184.1
 See application file for complete search history.

(56) References Cited

U.S. PATENT DOCUMENTS 6,153,639 A * 11/2000 Sternberg et al.
7,223,600 B2   5/2007 Berg et al.

FOREIGN PATENT DOCUMENTS

| WO | WO 93/14142 | 7/1993 |
| WO | WO-9411016 A1 | 5/1994 |
| WO | WO 95/03814 | 2/1995 |
| WO | WO 96/07432 | 3/1996 |
| WO | WO-97/34617 A1 | 9/1997 |

OTHER PUBLICATIONS

Lynch et al. Photochem, and Photobio. 49: 453-458, 1989.*
Lapes et al J. Photochem, and Photobio. B 36: 205-207, 1996.*
Stutes et al Basic & Chemical Immunol. pp. 694 and 703, 1987.*
Janeway, C., et al. ImmunoBiology, 1994. Current Biology Ltd. Philadelphia, PA; pp. 7.9-7.12 and 12.30-12.34.*
Canti, G., et al., "Antitumor immunity induced by photodynamic therapy with aluminum disulfonated phthalocyanines", *Anti-Cancer Drugs*, vol. 5, pp. 443-447, (1994).
de Vree, W.J., et al., "Evidence for an important role of neutrophils in the efficacy of photodynamic therapy in vivo", *Cancer Research*, vol. 56, pp. 2908-2911, (Jul. 1, 1996).
Korbelik, M., et al., "Photodynamic therapy-mediated immune response against Subcutaneous mouse tumors", *Cancer Research*, vol. 59, pp. 1941-1946, (Apr. 15, 1999).
Lee, S., et al., "Development of a polynucleotide vaccine from melanoma antigen recognized by T cells-1 and recombinant protein from melanoma antigen recognized by T cells-1 for melanoma vaccine clinical trials", *Journal of Immunotherapy*, vol. 23, No. 3, pp. 379-386, (2000).
Philip, R., et al., "Dendritic cells loaded with MART-1 peptide orinfected with adenoviral construct are functionally equivalent in the induction of tumor-specific cytotoxic T lymphocyte responses in patients with melanoma", *Journal of Immunotherapy*, vol. 23, No. 1, 168-176, (2000).
Wang, F., et al., "Phase I trial of a MART-1 peptide vaccine with incomplete Freund's adjuvant for resected high-risk melanoma", *Clinical Cancer Research*, vol. 5, pp. 2756-2765, (Oct. 1999).
Dougherty, Thomas.J. ,et al. ,"Review", *Photodynamic Therapy; Journal of the National Cancer Institute*, vol. 90, No. 12,(Jun. 17, 1998), 889-905.
Germain, Ronald.N. ,"MHC-Dependent Antigen Processing and Peptide Presentation: Providing Ligands for T Lymphocyte Activation", *Cell*. vol. 76, Lymphocyte Biology Section,(Jan. 28, 1994),287-299.
Hanlon, Douglas.J. ,et al. ,"Photoactivated 8-Methoxypsoralen Treatment Causes a Peptide-Dependent Increase in Antigen Display by Transformed Lymphocytes", *Publication of the International Union Against Cancer; Int. J. Cancer*: 78, XP-000946568,(Jan. 12, 1998),70-75.
Kirkin, Alexei.F. ,et al. ,"Establishment of gp100 and MART-1/ Melan-A-specific cytotoxic T lymphocyte clones using in vitro immunization against preselected highly immunogenic melanoma cell clones", *Cancer Immunol Immunother, Springer-Verlag 1999*, Received Dec. 16, 1988/Accepted Mar. 23, 1999,239-246.
Rock, Kenneth.L. ,et al. ,"A new foreign policy: MHC class I molecules monitor the outside world", *Review Imunology Today*, vol. 17,(Mar. 1996),131-137.
Schuler, G..,et al. ,"Commentary: Dendritic Cells as Adjuvants for Immune-mediated Resistance to Tumors", *Department of Dermatology; University of Erlangen-Nurnberg*; XP-002148419, J. Exp. Med The Rockefeller University Press; vol. 186, No. 8,(Oct. 20, 1997),1183-1187.
Specht, Jennifer.M. ,et al. ,"Dendritic Cells Retrovirally Transduced with a Model Antigen Gene Are Therapeutically Effective Against Established Pulmonary Metastases", *The Journal of Experimental Medicine*, vol. 186, No. 8,(Oct. 20, 1997),1213-1221.
Yewdell, Jonathan.W. ,et al. ,"Cell Biology of Antigen Processing and Presentation to Major Histocompatibility Complex Class I Molecule-Restricted T Lymphocytes", *Laboratory of Viral Diseases, National Institute of Allergy and Infections Diseases*, Advances in Immunology, vol. 52,(1992),1123.
Antunes, F , et al., "Apoptosis induced by exposure to low steady-state concentration of H2O2 is a consequence of lysosomal rupture", *Biochem J*., 356(Pt 2), (Jun. 1, 2001),549-55.
Helenius, A , et al., "Inhibition of Semliki forest virus penetration by lysosomotropic weak bases", *Journal of General Virology*, 58 (Pt.1), 1982 ,47-61.

(Continued)

*Primary Examiner* — Gerald R Ewoldt
(74) *Attorney, Agent, or Firm* — Schwegman, Lundberg & Woessner, P.A.

(57) ABSTRACT

The present invention provides a method of expressing an antigenic molecule or a part thereof on the surface of an antigen-presenting cell, said method comprising introducing a molecule into the cell cytosol by photochemical internalisation, wherein said molecule, or a part thereof, is subsequently presented on the surface of said cell. Methods of vaccination comprising this method, together with compositions comprising said cells and uses involving said cells expressing antigenic molecules are also provided.

14 Claims, 6 Drawing Sheets

OTHER PUBLICATIONS

Figure 1:
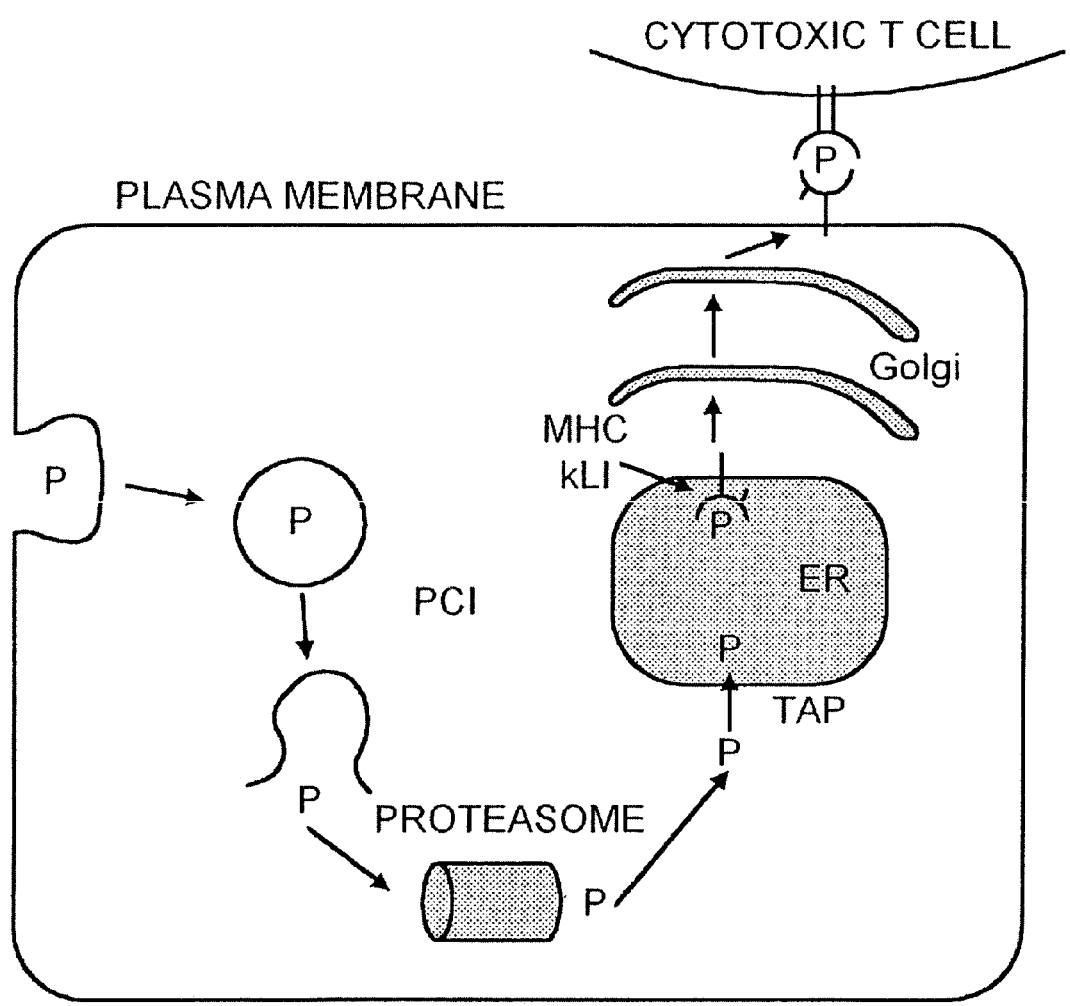

Styrt, B., et al., "Inhibition of neutrophil oxidative metabolism by lysosomotropic weak bases", *Blood*, 67(2), (Feb. 1986),334-42.

Zdolsek, J M., et al., "Photooxidative damage to lysosomes of cultured macrophages by acridine orange", *Photochem Photobiol.*, 51(1), (Jan. 1990),67-76.

Watson, James D., et al., "Molecular Biology of the Gene", *Molecular Biology of the Gene, Fourth Edition, The Benjamin/Cummings Publishing Company, Inc.*, 4 Pages pp. 880-881, 1987.

Nijman, H. W., et al., "T cell infiltration and MHC I and II expression in the presence of tumor antigens: An immunohistochemical study in patients with serous epithelial ovarian cancer", *Eur J obstet Gynecol Reprod Biol.*, 94(1), (Jan. 2001), 114-20.

Berg, K., et al., "Porphyrin-related photosensitizers for cancer imaging and therapeutic applications", *J Microsc.*, 218(Pt 2), (May 2005),133-47.

Dietze, A., et al., "Photochemical internalization (PCI): a new modality for light activation of endocytosed therapeuticals", *J Environ Pathol Toxicol Oncol.*, 25(1-2), (2006),521-36.

Salgaller, M. L., et al., "Immunization Against Epitopes in the Human Melanoma Antigen gp100 Following Patient Immunization With Synthetic Peptides", *Cancer Research*, 56, (1996),4749-4757.

Valmori, D., et al., "Enhanced Generation of Specific Tumor-Reactive CTL in Vitro by Selected Melan-A/MART-1 Immunodominant Peptide Analogues", *The Journal of Immunology*, 160, (1998),1750-1758.

Berg, K., et al., "Photochemical Internalization: A Novel Technology for Delivery of Macromolecules into Cytosol", *Cancer Research*, 59, (1999),1180-1183.

Berg, K., et al., "Photochemical Internalization: A New Tool for Drug Delivery", *Current Pharmaceutical Biotechnology*, 8(6), (2007),362-372.

Ditzel, H., et al., "Tumor Detection with $^{131}$I-labeled Human Monoclonal Antibody COU-1 in Patients with Suspected Colorectal Carcinoma", *Cancer Research*, 53(24), (1993),5920-5928.

Selbo, P. K., et al., "Photochemical Internalization of Therapeutic Macromolecular Agents: A Novel Strategy to Kill Multidrug-Resistant Cancer Cells", *The Journal of Pharmacology and Experminental Therapeutics*, 319(2), (2006), 604-612.

Selbo, P. K., et al., "Release of gelonin from endosomes and lysosomes to cytosol by photochemical internalization.", *Biochimlca et Biophysica Acta*, 1475(3), (2000),307-313.

Shiraishi, T., et al., "Photochemically enhanced cellular delivery of cell penetrating peptide-PNA conjugates.", *FEBS Letters*, 580(5), (2006),1451-1456.

Wilson, C. C., et al., "HIV-1-Specific CTL Responses Primed In Vitro by Blood-Derived Dendritic Cells and Th-1-Biasing Cytokines", *The Journal of Immunology*, 162, (1999), 3070-3078.

* cited by examiner

METHOD OF VACCINATION

The present invention relates to a method of vaccination which involves using photodynamic treatment (PDT) to introduce vaccine components into cells to achieve antigen presentation, and to vaccine compositions useful in such a method.

The majority of molecules do not readily penetrate cell membranes. Methods for introducing molecules into the cytosol of living cells are useful tools for manipulating and studying biological processes. Among the most commonly used methods today are microinjection, red blood cell ghost-mediated fusion and liposome fusion, osmotic lysis of pinosomes, scrape loading, electroporation, calcium phosphate and virus-mediated transfection. These techniques are useful for investigating cells in culture, although in many cases they may be impractical, time consuming, inefficient or they may induce significant cell death. Thus such techniques are not optimal for use in biological or medical research, or in therapies, where it is required that cells should remain viable and/or functional.

It is well known that porphyrins and many other photosensitizing compounds may induce cytotoxic effects on cells and tissues. These effects are based upon the fact that upon exposure to light the photosensitizing compound may become toxic or may release toxic substances such as singlet $O_2$ or other oxidising radicals which are damaging to cellular material or biomolecules, including the membranes of cells and cell structures, and such cellular or membrane damage may eventually kill the cells. These effects have been utilised in the treatment of various abnormalities or disorders, including especially neoplastic diseases. The treatment is named photodynamic therapy (PDT) and involves the administration of photosensitizing (photochemotherapeutic) agents to the affected area of the body, followed by exposure to photoactivating light in order to activate the photosensitizing agents and convert them into cytotoxic form, whereby the affected cells are killed or their proliferative potential diminished. Photosensitizing agents are known which will localise preferentially or selectively to the desired target site e.g. to a tumour or other lesion.

A range of photosensitizing agents are known, including notably the psoralens, the porphyrins, the chlorins and the phthalocyanins. Such drugs become toxic when exposed to light.

Photosensitizing drugs may exert their effects by a variety of mechanisms, directly or indirectly. Thus for example, certain photosensitisers become directly toxic when activated by light, whereas others act to generate toxic species, e.g. oxidising agents such as singlet oxygen or other oxygen-derived free radicals, which are extremely destructive to cellular material and biomolecules such as lipids, proteins and nucleic acids.

Porphyrin photosensitisers act indirectly by generation of toxic oxygen species, and are regarded as particularly favourable candidates for PDT. Porphyrins are naturally occurring precursors in the synthesis of heme. In particular, heme is produced when iron ($Fe^{3+}$) is incorporated in protoporphyrin IX (Pp) by the action of the enzyme ferrochelatase. Pp is an extremely potent photosensitizer, whereas heme has no photosensitizing effect. A variety of porphyrin-based or porphyrin-related photosensitisers are known in the art and described in the literature.

The cytotoxic effect is mediated mainly through the formation of singlet oxygen. This reactive intermediate has a very short lifetime in cells (<0.04 µs). Thus, the primary cytotoxic effect of PDT is executed during light exposure and very close to the sites of formation of $^1O_2$. $^1O_2$ reacts with and oxidizes proteins (histidine, tryptophan, methionine, cysteine, tyrosine), DNA (guanine), unsaturated fatty acids and cholesterol. One of the advantages of PDT is that tissues unexposed to light may be left unaffected ie. that a selective PDT effect may be obtained. There is extensive documentation regarding use of PDT to destroy unwanted cell populations, for example neoplastic cells. The patent literature describes a number of photodynamic compounds, alone or conjugated with targeting agents, e.g. immunoglobulins directed to neoplastic cell receptor determinants, making the complex more cell specific. Certain photochemical compounds, such as hematoporphyrin derivatives, have furthermore an inherent ability to localise in malignant cells. Such methods and compounds, are described in the Norwegian patent NO 173319, in Norwegian patent applications Nos. 90 0731, 176 645, 176 947, 180 742, 176 786, 301 981, 30 0499 and 89 1491.

In WO93/14142 a drug delivery system is described which comprises an anti-cancer agent and a photoactivatable agent (ie. a photosensitizer) attached to copolymeric carriers. Upon administration this complex enters the cell interior by pinocytosis or phagocytosis and locates inside the endosomes and lysosomes. In the lysosomes, the bond between the anti-neoplastic agent and the polymer is hydrolysed and the former can diffuse passively through the lysosome membrane into the cytosol. The utility of this method is thus limited to small molecular compounds which are able to diffuse across the lysosome membranes. After allowing a time lag for diffusion, a light source of appropriate wavelength and energy is applied to activate the photo-activatable compound. The combined effect of the anti-cancer agent and photoactivatable agent destroy the cell.

Such PDT methods as described above are thus directed to the destruction of cell structures leading to cell death.

WO 96/07432, on the other hand, is concerned with methods which use the photodynamic effect as a mechanism for introducing otherwise membrane-impermeable molecules into the cytosol of a cell in a manner which does not result in widespread cell destruction or cell death. In this method, the molecule is co-internalised (more particularly "endocytosed") into an intracellular vesicle in the cell (e.g. a lysosome or endosome) together with a photosensitizing agent. The cell is then exposed to photoactivating light which "activates" the photosensitizer, which in turn causes the vesicle membrane to disrupt or rupture, releasing the vesicle contents, including the molecule, into the cell interior ie. the cytosol. It was found that in such a method the functionality or the viability of the majority of the cells was not deleteriously affected. Thus, the utility of such a method, termed "photochemical internalisation" was proposed for transporting a variety of different molecules, including therapeutic agents, into the cytosol ie. into the interior of a cell.

We have now found that such a method can advantageously be used, not only to transfer molecules in the interior of a cell, but also to present or express them on a cell surface. Thus, following transport and release of a molecule into the cell cytosol, it may be transported to the surface of the cell where it may be presented on the outside of the cell ie. on the cell surface. Such a method has particular utility in the field of vaccination, where vaccine components ie. antigens or immunogens, may be introduced to a cell for presentation on the surface of that cell, in order to induce, facilitate or augment an immune response.

At its most general, the present invention thus provides a method of expressing an antigenic molecule or a part thereof on the surface of a cell, preferably an antigen-presenting cell, said method comprising introducing a molecule into the cell cytosol by photochemical internalisation, wherein said molecule, or a part thereof, is subsequently presented on the surface of said cell.

As used herein "expressing" or "presenting" refers to the presence of the molecule or a part thereof on the surface of said cell such that at least a portion of that molecule is exposed and accessible to the environment surrounding that cell. Expression on the "surface" may be achieved in which the molecule to be expressed is in contact with the cell membrane and/or components which may be present or caused to be present in that membrane.

Such antigenic presentation may advantageously result in the stimulation of an immune response, preferably an immune response which confers protection against subsequent challenge by an entity comprising or containing said antigen molecule or part thereof, and consequently the invention finds particular utility as a method of vaccination.

More particularly, this aspect of the invention provides a method of expressing an antigenic molecule or a part thereof on the surface of a cell, said method comprising:

contacting said cell with said antigenic molecule and with a photosensitizing agent, wherein said molecule and said agent are each taken up into an intracellular membrane-restricted compartment of said cell; and irradiating said cell with light of a wavelength effective to activate the photosensitizing agent, such that the membrane of said intracellular compartment is disrupted, releasing said molecule into the cytosol of the cell, without killing the cell, wherein, said released antigenic molecule, or a part thereof, is subsequently presented on the surface of said cell.

As used herein, a "disrupted" compartment refers to destruction of the integrity of the membrane of that compartment either permanently or temporarily, sufficient to allow release of the antigenic molecule contained within it.

Alternatively viewed, this aspect of the invention also provides a composition for use in expressing an antigenic molecule or a part thereof on the surface of a cell, preferably to simulate an immune response, said composition comprising an antigenic molecule and a photosensitizing agent. Preferably said composition is pharmaceutically acceptable and contains also a pharmaceutically acceptable excipient or diluent.

In a further aspect, the invention also provides the use of an antigenic molecule and a photosensitizing agent in the preparation of a medicament for use in expressing said antigenic molecule or a part thereof on the surface of a cell to stimulate an immune response.

A still further aspect of the invention provides a product comprising an antigenic molecule and a photosensitizing agent as a combined preparation for simultaneous, separate or sequential use in expressing said antigenic molecule or a part thereof on the surface of a cell, preferably to stimulate an immune response.

A yet further aspect of the invention provides a kit for use in expressing an antigenic molecule or a part thereof on the surface of a cell, said kit comprising a first container containing said antigenic molecule; and a second container containing a photosensitizing agent.

In the invention, the antigenic molecule may be any molecule wherein that molecule or a part thereof is capable of stimulating an immune response, when presented to the immune system in an appropriate manner. Advantageously, therefore the antigenic molecule will be a vaccine antigen or vaccine component, such as a polypeptide containing entity.

Many such antigens or antigenic vaccine components are known in the art and include all manner of bacterial or viral antigens or indeed antigens or antigenic components of any pathogenic species including protozoa or higher organisms. Whilst traditionally the antigenic components of vaccines have comprised whole organisms (whether live, dead or attenuated) ie. whole cell vaccines, in addition sub-unit vaccines, ie. vaccines based on particular antigenic components of organisms e.g. proteins or peptides, or even carbohydrates, have been widely investigated and reported in the literature. Any such "sub-unit"-based vaccine component may be used as the antigenic molecule of the present invention. However, the invention finds particular utility in the field of peptide vaccines. Thus, a preferred antigenic molecule according to the invention is a peptide (which is defined herein to include peptides of both shorter and longer lengths ie. peptides, oligopeptides or polypeptides, and also protein molecules or fragments thereof e.g. peptides of 5-500 e.g. 10 to 250 such as 15 to 75, or 8 to 25 amino acids). Parts of antigenic molecules which are presented or expressed preferably comprise parts which are generated by antigen-processing machinery within the cell. Parts may however be generated by other means which may be achieved through appropriate antigen design (e.g. pH sensitive bands) or through other cell processing means. Conveniently such parts are of sufficient size to generate an immune response, e.g. in the case of peptides greater than 5, e.g. greater than 10 or 20 amino acids in size.

A vast number of peptide vaccine candidates have been proposed in the literature, for example in the treatment of viral diseases and infections such as AIDS/HIV infection or influenza, canine parvovirus, bovine leukaemia virus, hepatitis, etc. (see e.g. Phanuphak et al., Asian Pac. J. Allergy. Immunol. 1997, 15(1), 41-8; Naruse, Hokkaido Igaku Zasshi 1994, 69(4), 811-20; Casal et al., J. Virol., 1995, 69(11), 7274-7; Belyakov et al., Proc. Natl. Acad. Sci. USA, 1998, 95(4), 1709-14; Naruse et al., Proc. Natl. Sci. USA, 1994 91(20), 9588-92; Kabeya et al., Vaccine 1996, 14(12), 1118-22; Itoh et al., Proc. Natl. Acad. Sci. USA, 1986, 83(23) 9174-8. Similarly bacterial peptides may be used, as indeed may peptide antigens derived from other organisms or species.

In addition to antigens derived from pathogenic organisms, peptides have also been proposed for use as vaccines against cancer or other diseases such as multiple sclerosis. For example, mutant oncogene peptides hold great promise as cancer vaccines acting an antigens in the simulation of cytotoxic T-lymphocytes. (Schirrmacher, Journal of Cancer Research and Clinical Oncology 1995, 121, 443-451; Curtis Cancer Chemotherapy and Biological Response Modifiers, 1997, 17, 316-327). A synthetic peptide vaccine has also been evaluated for the treatment of metastatic melanoma (Rosenberg et al., Nat. Med. 1998, 4(3), 321-7). A T-cell receptor peptide vaccine for the treatment of multiple sclerosis is described in Wilson et al., J. Neuroimmunol. 1997, 76(1-2), 15-28. Any such peptide vaccine component may be used as the antigenic molecule of the invention, as indeed may any of the peptides described or proposed as peptide vaccines in the literature. The peptide may thus be synthetic or isolated or otherwise derived from an organism.

The cell which is subjected to the methods, uses etc. of the invention may be any cell which is capable of expressing, or presenting on its surface a molecule which is administered or transported into its cytosol.

Since the primary utility of the invention resides in antigen-presentation or vaccination, the cell is conveniently an immune effector cell ie. a cell involved in the immune response. However, other cells may also present antigen to the immune system and these also fall within the scope of the invention. The cells according to the present invention are thus advantageously antigen-presenting cells. The antigen-presenting cell may be involved in any aspect or "arm" of the immune response, including both humoral and cell-mediated immunity, for example the stimulation of antibody production, or the stimulation of cytotoxic or killer cells, which may recognise and destroy (or otherwise eliminate) cells expressing "foreign" antigens on their surface. The term "stimulating an immune response" thus includes all types of immune responses and mechanisms for stimulating them.

The stimulation of cytotoxic cells or antibody-producing cells, requires antigens to be presented to the cell to be stimulated in a particular manner by the antigen-presenting cells, for example MHC Class I presentation (e.g. activation of $CD8^+$ cytotoxic T-cells requires MHC-1 antigen presentation).

Antigen-presenting cells are known in the art and described in the literature and include for example, lymphocytes (both T and B cells), dendritic cells, macrophages etc. Others include for example cancer cells e.g. melanoma cells.

For antigen presentation by an antigen-presenting cell to a cytotoxic T-cell (CTL) the antigenic molecule needs to enter the cytosol of the antigen-presenting cell (Germain, Cell, 1994, 76, 287-299). The present invention provides an efficient means of delivery of the antigenic molecule into the cytosol.

Once released in the cell cytosol by the photochemical internalisation process, the antigenic molecule may be processed by the antigen-processing machinery of the cell and presented on the cell surface in an appropriate manner e.g. by Class I MHC. This processing may involve degradation of the antigen, e.g. degradation of a protein or polypeptide antigen into peptides, which peptides are then complexed with molecules of the MHC for presentation. Thus, the antigenic molecule expressed or presented on the surface of the cell according to the present invention may be a part or fragment of the antigenic molecule which is internalised (endocytosed).

Antigens may be taken up by antigen-presenting cells by endocytosis and degraded in the endocytic vesicles to peptides. These peptides may bind to MHC class II molecules in the endosomes and be transported to the cell surface where the peptide-MHC class II complex may be recognised by CD4+ T helper cells and induce an immune response. Alternatively, proteins in the cytosol may be degraded, e.g. by proteasomes and transported into endoplasmic reticulum by means of TAP (transporter associated with antigen presentation) where the peptides may bind to MHC class I molecules and be transported to the cell surface as illustrated in the FIG. 1 (Yewdell and Bennink, 1992, Adv. Immunol. 52: 1-123). If the peptide is of foreign antigen origin, the peptide-MHC class I complex will be recognised by CD8+ cytotoxic T-cells (CTLs). The CTLs will bind to the peptide-MHC (HLA) class I complex and thereby be activated, start to proliferate and form a clone of CTLs. The target cell and other target cells with the same peptide-MHC class I complex on the cells surface may be killed by the CTL clone. Immunity against the foreign antigen may be established if a sufficient amount of the antigen can be introduced into the cytosol (Yewdell and Bennink, 1992, supra; Rock, 1996, Immunology Today 17: 131-137). This is the basis for development of inter alia cancer vaccines. One of the largest practical problems is to introduce sufficient amounts of antigens (or parts of the antigen) into the cytosol. This may be solved according to the present invention by PCI. This principle is illustrated in FIG. 1, which shows how PCI can be utilised to stimulate CTLs. A peptide or protein (P) is applied extracellularly to antigen-presenting cells. P is endocytosed and released into cytosol by PCI. The peptide or protein will thereafter be partly degraded by proteasomes and transported to the cells surface complexed to MHC (HLA) class I where the complex can be recognised by CTLs.

As will be described in more detail in the Examples below, it has been demonstrated that photochemical internalisation may be used efficiently according to the present invention for cytosolic delivery of cancer-specific peptides.

The antigenic molecule and/or photosensitivity agent may be targeted to specific cells or tissues by employing targeting agents e.g. target-specific delivery or carrier systems or carrier molecules. Thus for example the antigenic molecule and/or photosensitising agent may be delivered to the cell using a vector or carrier system e.g. reconstituted LDL-particles. The carrier molecule may be bound or conjugated to the antigenic molecule, to the photosensitising agent or both, and the same or different carrier molecules may be used. The antigenic molecule and/or photosensitising agent may also be conjugated to a site-targeting ligand, such as a ligand which is specific for particular cell-types or particular cell structures e.g. an antibody recognising a surface antigen expressed on certain cell types e.g. a tumour-specific antigen. Such mechanisms may act to increase uptake of the photosensitiser and/or antigen molecule through receptor-mediated endocytosis. Such targeting molecules carriers or vectors may also be used to direct the antigenic molecule and/or photosensitising agent to the intracellular compartment.

The intracellular membrane-restricted compartment may be any such compartment which is present in a cell. Preferably the compartment will be a membrane vesicle, especially an endosome or a lysosome. However, the intracellular compartment may also include the Golgi apparatus or the endoplasmic reticulum. All that is required is that the antigenic molecule and the photosensitising agent locate to the same intracellular compartment(s).

The photochemical internalisation process is described in more detail in WO 96/07432 (the contents of which are incorporated herein by reference). Methods of PDT are also now widely described in the literature.

The photosensitizing agent to be used according to the present invention may be any such agent which localises to intracellular compartments, particularly endosomes or lysosomes. A range of such photosensitising agents are known in the art and are described in the literature, including in WO96/07432. Mention may be made this respect of di- and tetrasulfonated aluminium phthalocyanine, sulfonated tetraphenylporphines ($TPPS_n$), nile blue, chlorin $e_6$ derivatives, uroporphyrin I, phylloerythrin, haematoporphyrin and methylene blue which have been shown to locate in endosomes and lysosomes of cells in culture. This is in most cases due to endocytic activity.

Classes of suitable photosensitising agent which may be mentioned thus include porphyrins, phthalocyanines, purpurins, chlorins, benzoporphyrins naphthalocyanines, cationic dyes, tetracyclines and lysomotropic weak bases or derivatives thereof (Berg et al., Photochemistry and Photobiology, 1997, 65, 403-409).

Preferred photosensitising agents include $TPPS_4$ (Zabner et al., J. Biol. Chem. 1995, 270, 18997-19007) $TPPS_{2a}$ and $AlPcS_{2a}$.

The following abbreviations are used: $AlPcS_{2a}$ for aluminum phthalocyanine with 2 sulfonate groups on adjacent phenyl rings; $TPPS_4$ for meso-tetraphenylporphine with 4 sulfonate groups; $TPPS_{2a}$ for meso-tetraphenylporphine with 2 sulfonate groups on adjacent phenyl rings.

The photochemical internalisation according to the present invention may be carried out using PDT methods which are known and standard in the art and appropriate modifications of such techniques which are effective in this method. Thus, the antigenic molecule and photosensitising agent may be delivered to the cell by application or administration according to methods and means known in the art of PDT.

The methods of the present invention may be used in vitro or in vivo, either by in situ treatment or by ex vivo treatment, followed by administration of the treated cells.

Thus, a further aspect of the invention provides an antigen-presenting cell expressing an antigenic molecule, or a part thereof, on its surface, which cell is obtainable (or obtained) by a method as hereinbefore defined. Other aspects of the invention provide a population or culture of such cells, especially a viable and functionally intact population or culture of such cells, and also the use of such a cell (or population or culture of cells) in therapy, particularly for stimulating an immune response, and especially for stimulating CTLs.

Also provided is the use of such a cell (or population or culture of cells) for the preparation of a medicament (e.g. a vaccine composition) for stimulating an immune response, and especially for stimulating CTLs.

In vivo, any mode of administration common or standard in the art may be used, e.g. injection, infusion, topical administration, both to internal and external body surfaces etc. For in vivo use, the invention can be used in relation to any tissue which contains the target cells, including body fluid locations, as well as solid tissues. All tissues can be treated as long as the photosensitises is taken up by the target cells, and the light can be properly delivered.

Thus, the compositions of the invention may be formulated in any convenient manner according to techniques and procedures known in the pharmaceutical art, e.g. using one or more pharmaceutically acceptable carrier or excipients. The nature of the composition and carriers or excipient materials, dosages etc. may be selected in routine manner according to choice and the desired route of administration, purpose of vaccination etc. Dosages may likewise be determined in routine manner and may depend upon the nature of the antigenic molecule, purpose of vaccination, age of patient, mode of administration etc., in connection with the photosensitising agent the potency/ability to disrupt membranes on irradiation, should also be taken into account.

The light irradiation step to activate the photosensitising agent may likewise take place according to techniques and procedures well known in the art. For example, the wavelength and intensity of the light may be selected according to the photosensitising agent used. Suitable light sources are well known in the art.

As mentioned earlier, and as described in WO96/07432, it has been found that photochemical internalisation in this manner does not deleteriously affect the viability and functionality of the cells. In particular, it has been found that when a population or plurality of cells is treated according to the present invention, a majority of the cells are not killed, and survive the treatment, substantially functionally intact.

As used herein, the term "without killing the cell" is intended to define such a situation. In other words in a population or plurality of cells, substantially all of the cells, or a significant majority (e.g. at least 75%, more preferably at least 80, 85, 90 or 95% of the cells) are not killed.

Clearly when dealing with the light irradiation of a population or a plurality of cells it is possible that certain groups of cells or certain areas of tissue may receive more light or in some other way be subjected to a larger PCI effect that other groups of cells or areas of tissue. Thus, the percentage values given for cell survival are not necessarily uniform across the entire irradiated population and refer to the percent of viable cells which remain in the irradiated population, the requirement being only that a sufficient portion of the irradiated cells survive. In addition, cell death induced by irradiation may take some time, e.g. a number of hours to occur. In this case it can be seen that cells which eventually die might also be able to express an antigenic molecule on their surface in accordance with the methods of the present invention and may thus be involved in the methods, uses etc. of the present invention. Thus the % cell death refers to the percent of cells which remain viable within a few hours of irradiation (e.g. up to 4 hours after irradiation) but preferably refers to the % viable cells 4 or more hours after irradiation.

The methods of the invention may be modified such that the fraction or proportion of the surviving cells is regulated by selecting the light dose in relation to the concentration of the photosensitivity agent. Again, such techniques are known in the art.

The present invention provides an efficient means for delivery of a large variety of antigenic molecules. The invention has a number of features rendering it particularly suitable as a vaccine delivery tool: 1) it has no restrictions on the size of the molecule to be delivered as long as the molecule can be endocytosed by the target cell; 2) it is not dependent on cell proliferation; 3) it is site specific in that only areas exposed to light are affected; 4) it is not oncogenic. In addition, photochemical internalisation may potentially be combined with other principles for generating site or tissue specific drug action, such as targeting by the use of specific ligands for cell surface structures, employing regulatory gene elements that confer tissue specificity or the use of disease-specific drugs, opening a possibility of obtaining substantially synergistic effects in the specificity of drugs for target cells.

The invention will now be described in more detail in the following non-limiting Examples with reference to the following drawings in which:

FIG. 1 shows a schematic representation of how PCI can be utilised to stimulate CTLs. A peptide or protein (P) is applied extracellularly to antigen presenting cells. P is endocytosed and released into cytosol by PCI. The peptide or protein will thereafter be partly degraded by proteasomes and transported to the cells surface complexed to MHC (HLA) class I where the complex can be recognised by CTLs.

Figure 2:
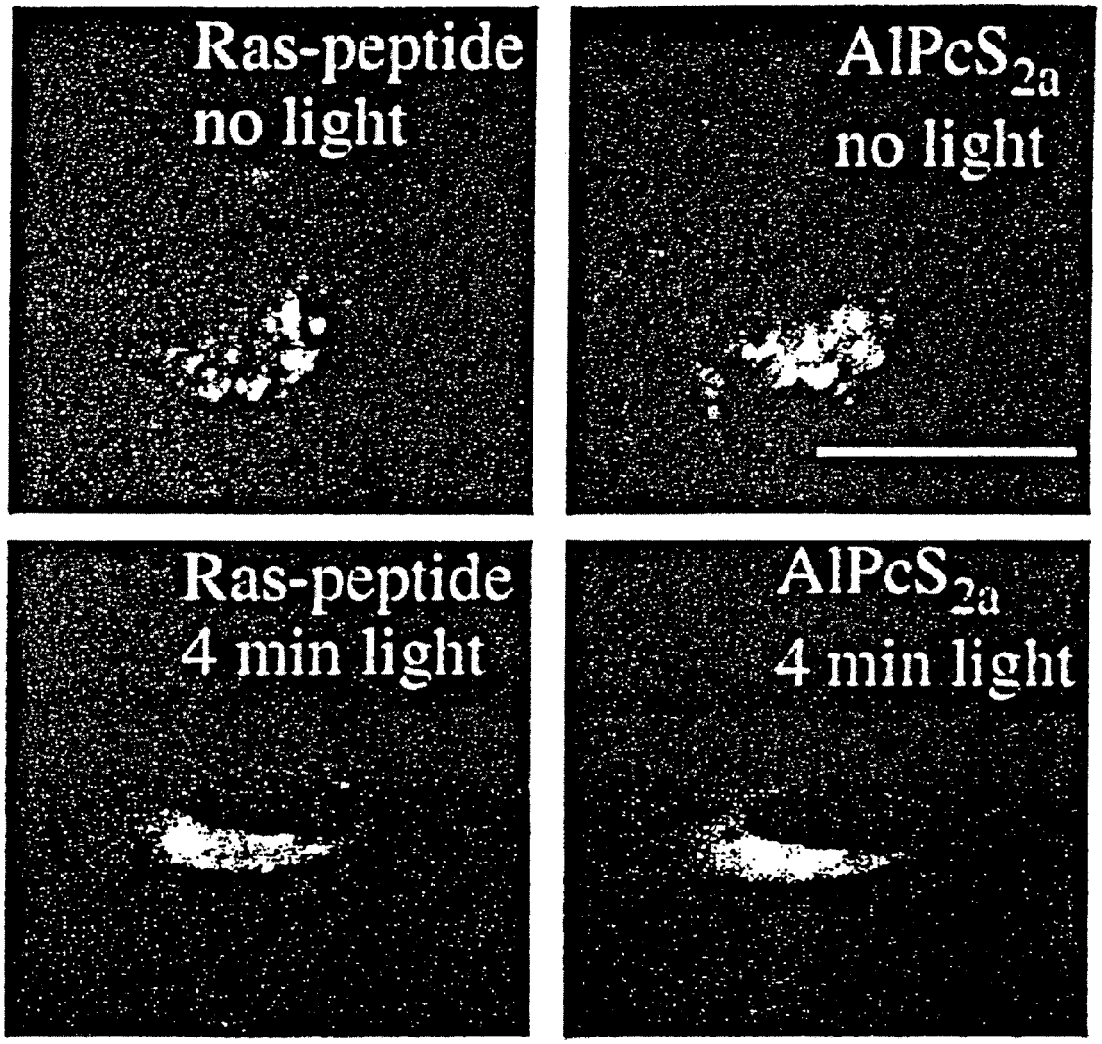

FIG. 2 shows photochemically induced relocalisation of a peptide. BL2-G-E6 cells were incubated with a fluorescein-labelled p21$^{ras}$-derived 5-21, Val$^{12}$ peptide and AlPcS$_{2a}$. The cells were examined for fluorescein-peptide and AlPcS$_{2a}$ localisation by fluorescence microscopy before (top panels) and 30 minutes after (bottom panels) a 4-min exposure to red light. Bar 20 μm.

Figure 3:
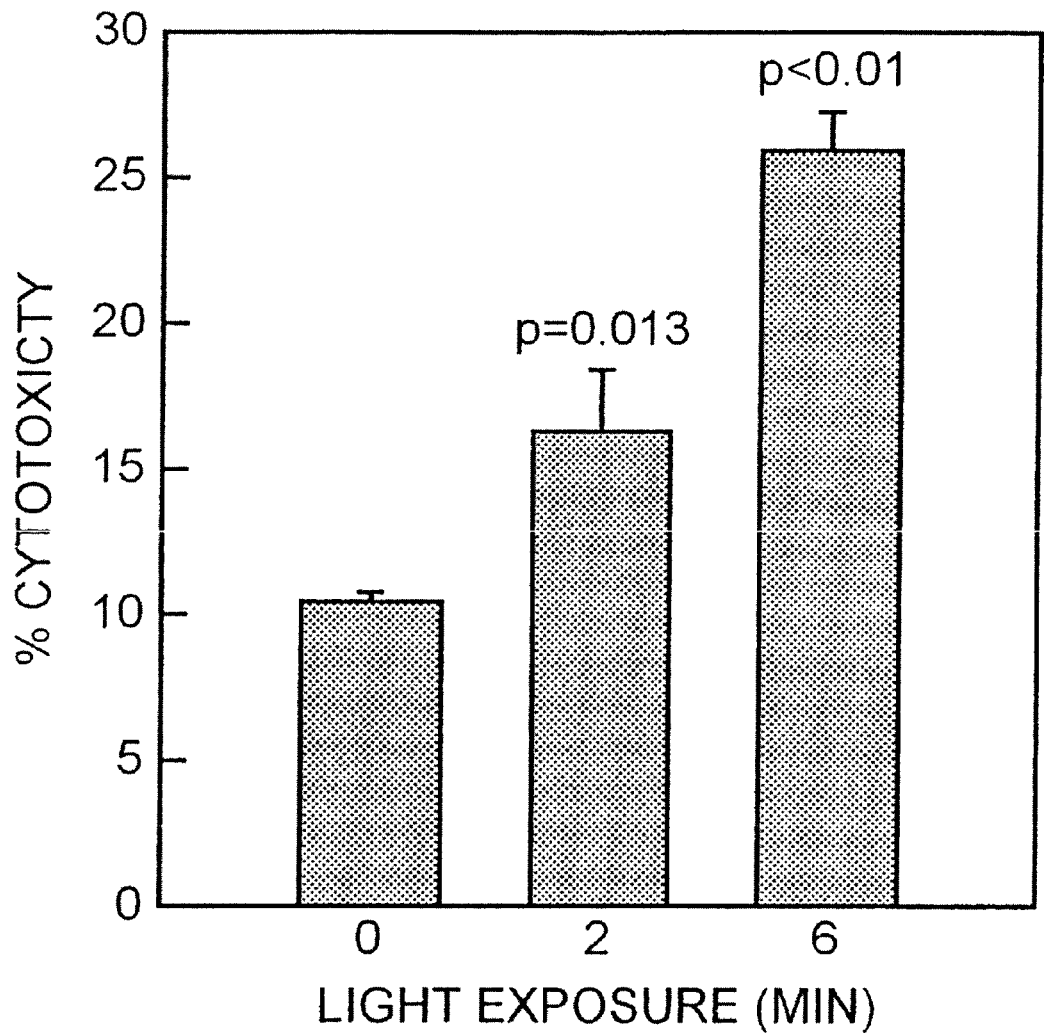

FIG. 3 shows the cytotoxicity of a CD8$^+$ T lymphocyte clone against FM3 melanoma cells after PCI of a MART-1 peptide.

Figure 4:
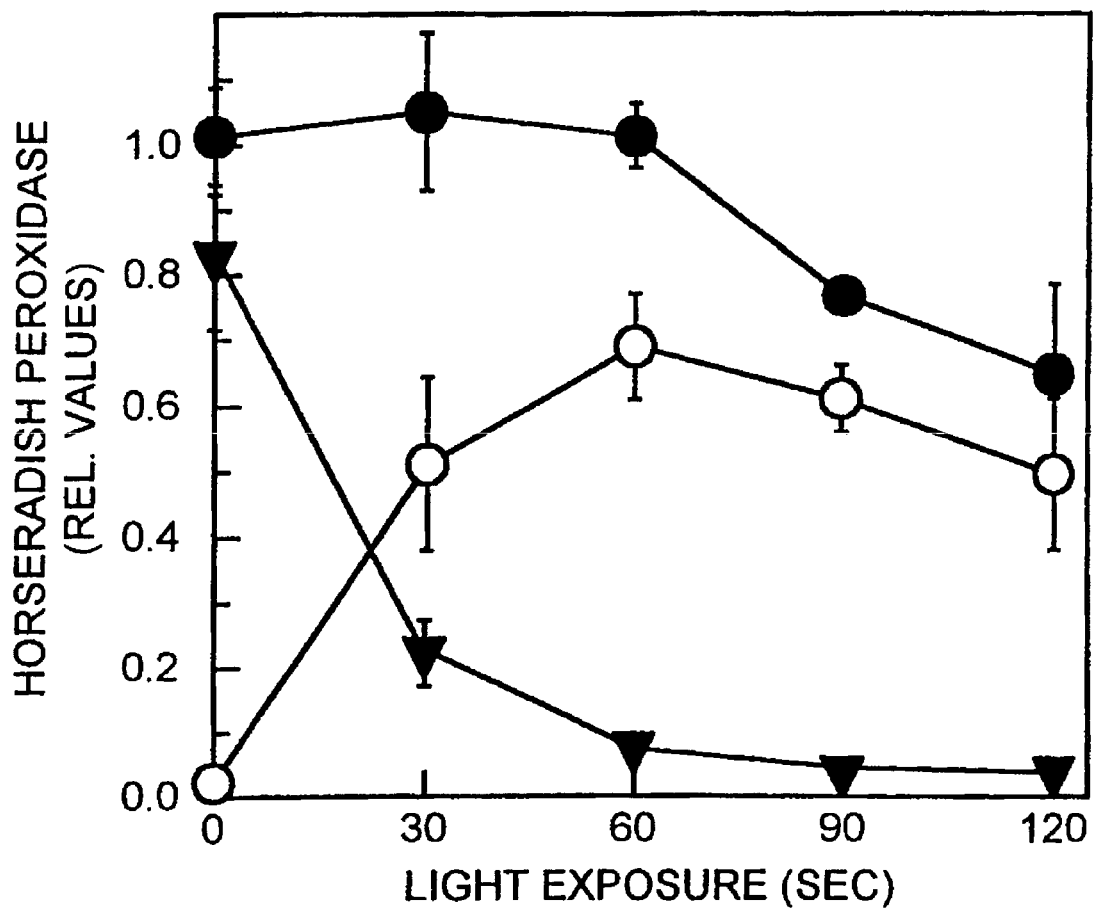

FIG. 4 shows the ability of PCI to deliver HRP into the cytosol. NHIK 3025 cells were treated with 3.2 ug/ml TPPS$_{2A}$ and 1 mg/ml HRP for 18 hours. The medium was then replaced with drug-free medium before exposure to the indicated light doses. HRP activity was measured in intact cells (●) and in cytosol (○) separated from cytosol-free cell corpses (♥) by electropermeabilisation and a density centrifugation technique.

Figure 5A:
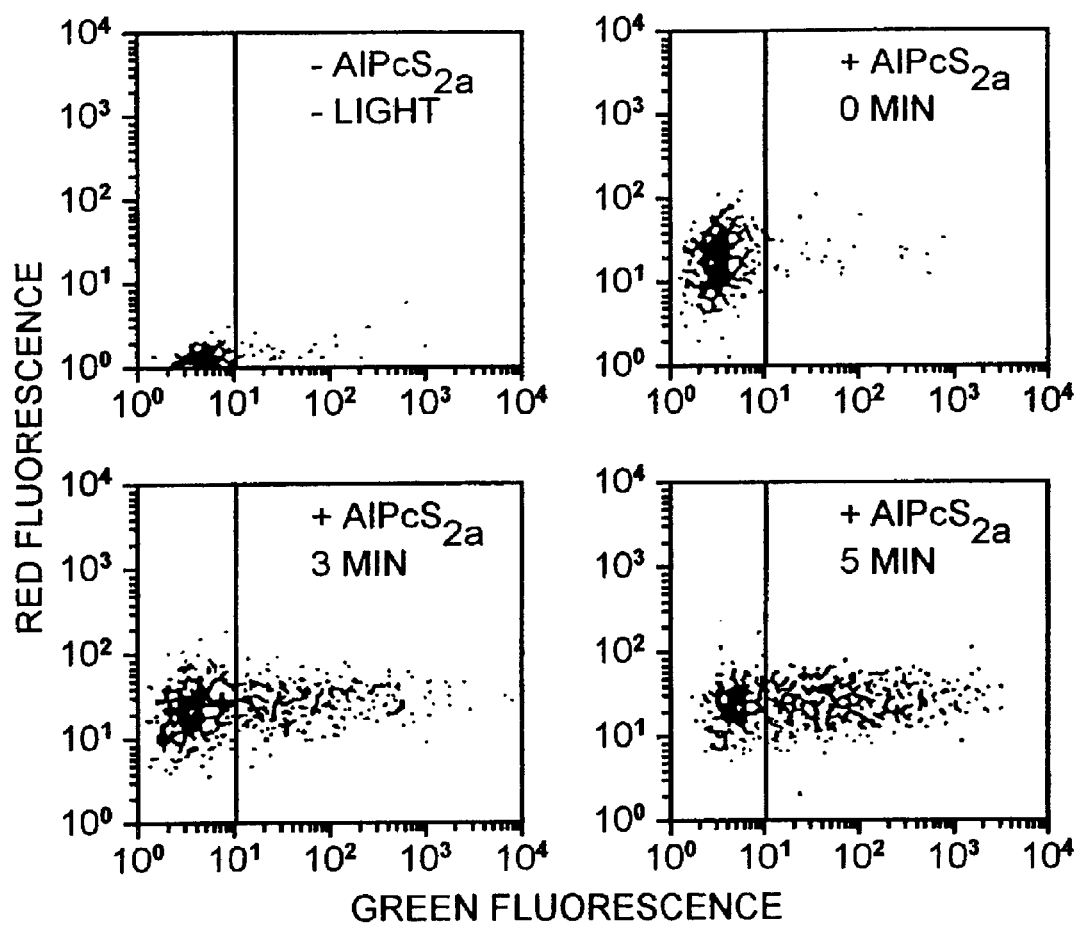

FIG. 5 shows photochemically induced expression of GFP. a. expression of GFP in THX cells treated with pEGFP-N1-pLys complex in the absence of AlPcS$_{2a}$ and light or in the presence of AlPcS$_{2a}$ followed by exposure to light as indicated on the figure. The cells were analysed by flow cytometry, reckoning the cells on the right side of the drawn line as positive for GFP expression. b. expression of GFP in THX cells treated for 18 hours with a photosensitiser (20 μg/ml AlPcS$_{2a}$ or 0.25 µg/ml 3-THPP) followed by a 6 hour transfection with pEGF-N1-pLys complex and exposure to light inactivating 50% of the cells. GFP expression was analysed by flow cytometry as described in a.

EXAMPLES

Materials and Methods

Irradiation

Two different light sources were used for treatment of the cells, both consisting of a bank of 4 fluorescent tubes. Cells treated with TPPS$_4$, TPPS$_{2a}$, and 3-THPP (Porphyrin Products, Logan, Utah) were exposed to blue light (model 3026; Appl. Photophysics, London, UK) with a light intensity reaching the cells of 1.5 mW/cm$^2$ while cells treated with AlPcS$_{2a}$ (Porphyrin Products, Logan, Utah) were exposed to red light (Philips TL 20W/09) filtered through a Cinemoid 35 filter with a light intensity reaching the cells of 1.35 mW/cm$^2$.

Fluorescence Microscopy

The cells were analysed by fluorescence microscopy as described in Berg. K., et al., Biochem. Biophys. Acta., 1370: 317-324, 1998. For analysis of fluorescein-labelled molecules the microscope was equipped with a 450-490 nm excitation filter, a 510 nm dichroic beam splitter and a 510-540 nm band pass emission filter.

Preparation of Plasmid-pLys Complexes and Treatment of Cells

Plasmid-pLys complexes (charge ratio, 1.7) were prepared by gently mixing 5 µg plasmid (pEGFP-N1; Clontech Laboratories, Inc., Palo Alto, Calif.) in 75 µl of HBS with 5.3 µg pLys (MW 20700; Sigma, St. Louis, Mo.) in 75 µl of HBS. The solutions were incubated for 30 min at room temperature, diluted with culture medium and added to the cells.

THX cells were incubated with 20 µg/ml AlPcS$_{2a}$ for 18 hours at 37° C., washed and incubated in sensitizer-free medium for 3 hours before incubation with plasmid-pLys complexes for 2 hours. The pEGFP-N1/pLys treated THX cells were washed once and incubated for 2 hours in culture medium without additions before exposure to light. The cells were incubated at 37° C. for 2 days, subcultured and further incubated for an additional 5 days before analysis of GFP expression by flow cytometry.

HCT-116 cells were incubated with 20 µg/ml AlPcS$_{2a}$ for 18 hours, washed and transfected with plasmid-pLys complexes for 6 hours before light exposure in plasmid-free medium. After 40 hours incubation at 37° C. the GFP expression was studied by microscopy.

Flow Cytometry Analysis

The cells were trypsinised, centrifuged, resuspended in 400 µl of culture medium and filtered through a 50 µm mesh nylon filter. The cells were then analysed in a FACStar plus flow cytometer (Becton Dickinson). Green Fluorescent Protein (GFP) was measured through a 510-530 nm filter after excitation with an argon laser (200 mW) tuned on 488 nm. AlPcS$_{2a}$ was measured through a 650 nm longpass filter after excitation with a krypton laser (50 mW) tuned on 351-356 nm. Cell doublets were discriminated from single cells by gating on the pulse width of the GFP fluorescence signal. The data were analysed with PC Lysys II software (Becton Dickinson).

Preparation of Fluorescein-Peptide and Treatment of Cells

The fluorescein-labelled Val$^{12}$-p21$^{ras}$-peptide (residues 5-21) were synthesised and provided by Alan Cuthbertson, Nycomed Amersham).

BL2-G-E6 cells were incubated with 30 µg/ml of the fluorescein-labelled p21$^{ras}$-derived peptide for 18 hours followed by 20 µg/ml AlPcS$_{2a}$ for 18 hours and 1 hour in drug-free medium before exposure to red light.

Example 1

Photochemical Internalisation (PCI) can be used to Enable Peptides to Enter the Cytosol of Cells To evaluate PCI for cytosolic delivery of cancer-specific peptides, a fluorescein-labelled p21$^{ras}$ peptide encompassing residues 5-21 and containing a Val$^{12}$ mutation (G12V) was used (Gjertsen, M. K., et al., Int. J. Cancer, 72: 784-790, 1997). In BL2-6-E6 mouse fibroblasts, the ras peptide colocalised well with AlPcS$_{2a}$, indicating endocytic uptake of the peptide (FIG. 2). After a 4-min exposure to light, the fluorescein-labelled ras peptide and AlPcS$_{2a}$ were found to be located diffusely in the cytoplasm. Similar effects were not observed in cells exposed to the fluorescein-labelled ras peptide and light only (data not shown).

Example 2

Use of PCI to Induce Antigen Presentation and CD8$^+$ T Lymphocyte Mediate Cell Killing FM3 melanoma cells (2×10$^5$/well in 6 well plates), grown in RPMI 1640 medium with 10% foetal calf serum (FCS), not expressing MART-1 peptide were treated with 10 µg/ml of the photosensitising agent AlPcS$_{2a}$ for 18 hours. The cells were then released from the substratum with EDTA (0.1 M) in Dulbecco's phosphate-buffered saline (PBS) and kept in solution during loading of the cells with $^{51}$Cr (60 µCi/ml Na$_2$CrO$_4$) for 1 hour in 100% FCS followed by 5 hours incubation with 5 µg/ml MART-1 peptide in RPMI 1640 in 10% FCS, while the cells were still kept in solution. The sequence of the MART-1 peptide was: TAEEAAGIG-ILTVILG (SEQ ID NO:1). The cells were then washed twice in RPMI 1640 medium containing 10% FCS and seeded out in 96-well plates (2000/well in 100 µl medium (RPMI 1640/10% FCS). The cells were then exposed to light for the times as indicated in FIG. 3 ((Philips TL 20W/09) filtered through a Cinemoid 35 filter with a light intensity reaching the cells of 1.35 mW/cm$^2$ (Rodal et al., 1998, J. Photochem. Photobiol. B: Biol. 45: 150-9)). 18 hours after light exposure the medium was removed and medium containing MART-1/HLA-A2 specific cytotoxic T lymphocytes (CTLs—40,000/well added in 100 µl) were added. After 4 hours of incubation the medium was separated from FM3 cells and the $^{51}$Cr released to the medium (as an indicator of lysed cells) was counted as well as the spontaneous and maximum release as previously described (Fossum et al., 1995, Cancer Immunol. Immunother. 40: 165-172). The percentage specific chromium release was calculated by the formula: (experimental release–spontaneous release)/(maximum release–spontaneous release)×100. It can be seen from the results shown in FIG. 3 that FM3 cells after PCT of a MART-1 peptide as outlined above show light dependent susceptibility to CDS$^+$ T lymphocyte cytotoxicity.

Example 3

PCI Induces the Release of a Large Fraction of the Endocytosed Molecule

This was shown by PCI induced internalisation/endocytosis of Horseradish Peroxidase (HRP).

By using HRP, it is demonstrated (see FIG. 4) that PCI induces the release of a large fraction (>60%) of endocytosed HRP into the cytosol.

In this experiment NHIK 3025 cells (carcinoma cells in situ from human cervix) were treated with the photosensitising agent TPPS$_{2a}$ (3.2 μg/ml) and 1 mg/ml HRP for 18 hours. The medium was then replaced with drug free medium before exposure to the light doses as indicated in FIG. 4. HRP activity was measured according to the procedure described in Steinman et al., J. Cell Biol., 68: 665-687, 1976. Cytosol was separated from cytosol-free cell corpses by electropermeabilisation and a density centrifugation technique (Berg et al., Int. J. Cancer 59: 814-822, 1994).

Example 4

PCI can be Used to Enhance the Delivery of Functional Genes

Figure 5B:
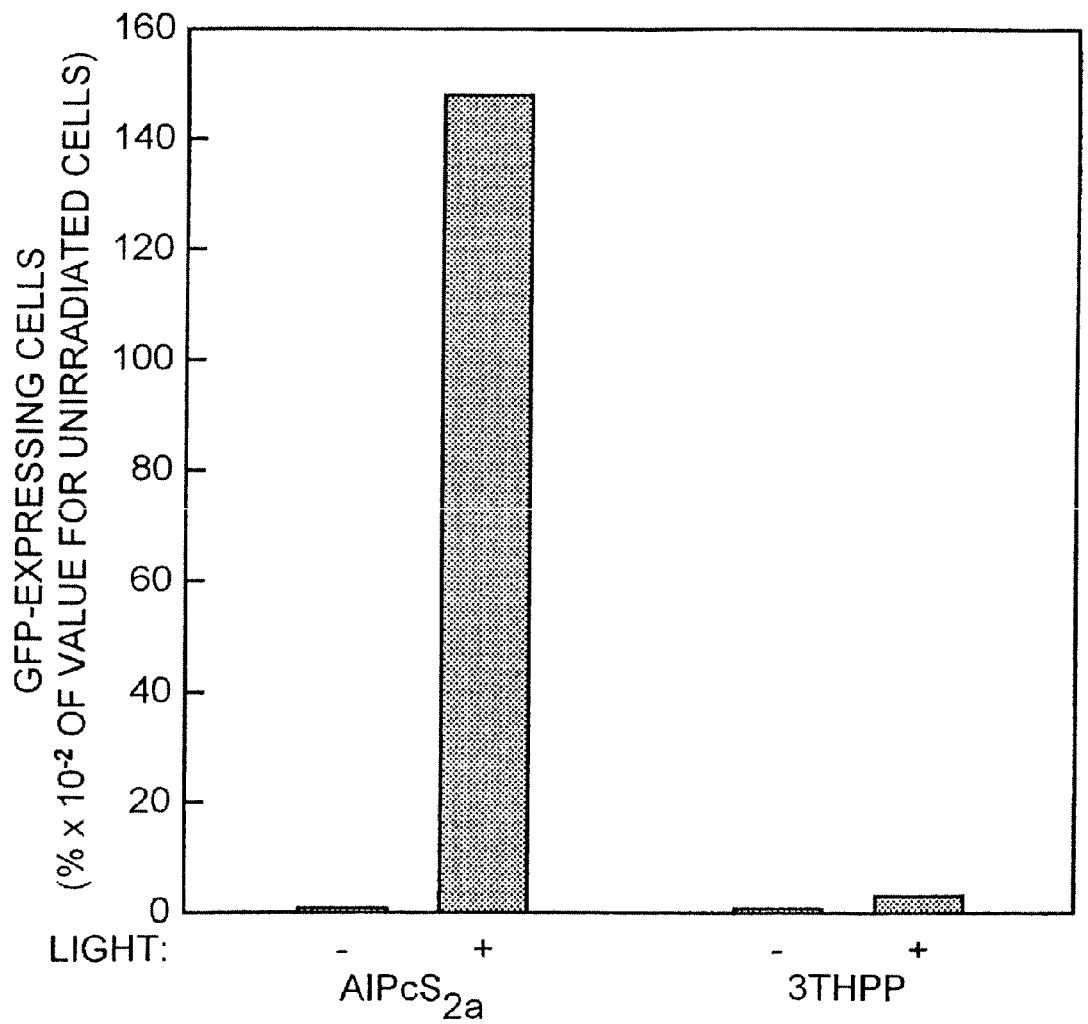

To demonstrate this, THX cells were transfected with a pLys-complex of a plasmid (pEGFP-N1) coding for green fluorescent protein (GFP). The expression of GFP was analysed by flow cytometry (FIGS. 5a and b) and fluorescence microscopy (data not shown). As can be seen from FIG. 5a, treatment with AlPcS$_{2a}$ and light led to a strong increase in the percentage of the cells expressing GFP. The fraction of the cells that was positive for this reporter molecule increased from 1% at no light treatment to 50% after a 5-min light exposure. GFP expression was not enhanced by light in cells treated with pEGFP-pLys in the absence of a photosensitiser. A complex of an irrelevant plasmid (encoding heme oxygenase) and pLys did not induce green fluorescence when combined with AlPcS$_{2a}$ and light (data not shown). Consequently, in a light-directed manner, PCI can substantially increase the efficiency of transfection of a functional gene to THX cells. Similar results were obtained using TPPS$_{2a}$ as a photosensitiser and BHK-21 and HCT-116 as target cells (data not shown). The essentially non-lysosomally located sensitiser 3-THPP induced only a minor increase in GFP expression (FIG. 5b). PCI of pEGFP-N1 not complexed with pLys did not induce the expression of GFP (data not shown).

irradiating said cell ex vivo with light of a wavelength effective to activate the photosensitizing agent, such that the membrane of said intracellular compartment is disrupted, releasing said peptide into the cytosol of the cell, without killing the cell;

wherein said released antigenic peptide, or a part thereof of sufficient size to stimulate a cytotoxic T cell response, is subsequently presented on the surface of said cell by a class I MHC molecule;

administering the cell to a mammal after irradiating said cell to thereby stimulate the in vivo immune response to the antigenic peptide; and wherein the photosensitizing agent is selected from the group consisting of a porphyrin, phthalocyanine and a chlorin.

2. The method of claim 1, wherein the antigenic peptide is a vaccine antigen or vaccine component.

3. The method of claim 1 wherein the photosensitizing agent is meso-tetraphenylporphine with 4 sulfonate groups (TPPS$_4$), meso-tetraphenylporphine with 2 sulfonate groups on adjacent phenyl rings (TPPS$_{2a}$), or aluminum phthalocyanine with 2 sulfonate groups on adjacent phenyl rings (AlPcS$_{2a}$).

4. The method of claim 1, wherein the antigenic peptide and/or photosensitizing agent is bound to one or more targeting agents or carrier molecules.

5. The method of claim 1, wherein at least 90% of the cells are not killed.

6. The method of claim 1, wherein at least 95% of the cells are not killed.

7. The method of claim 1, wherein the photosensitizing agent is a sulfonated tetraphenylporphine, a disulfonated aluminum phthalocyanine or a tetrasulfonated aluminum phthalocyanine.

8. A method of stimulating a CD8$^+$ cytotoxic T cell immune response to an antigenic peptide in vivo, said method comprising:

contacting an antigen presenting cell selected from a macrophage and a dendritic cell in a patient with an antigenic peptide and with a photosensitizing agent in vivo,

The invention claimed is:

1. A method of stimulating a CD8$^+$ cytotoxic T cell immune response to an antigenic peptide in vivo, said method comprising:

contacting an antigen presenting cell selected from a macrophage and a dendritic cell with said antigenic peptide and with a photosensitizing agent ex vivo, wherein said peptide and said agent are each taken up into an intracellular membrane-restricted compartment of said cell;

wherein said peptide and said agent are each taken up into an intracellular membrane-restricted compartment of said cell;

irradiating said cell with light of a wavelength effective to activate the photosensitizing agent, such that the membrane of said intracellular compartment is disrupted, releasing said peptide into the cytosol of the cell, without killing the cell;

wherein said released antigenic peptide, or a part thereof of sufficient size to stimulate a cytotoxic T cell response, is subsequently presented on the surface of said cell by a class I MHC molecule;

wherein presentation of the antigenic peptide, or part thereof, on the surface of said cell results in stimulation of the immune response specific for said antigenic peptide or a part thereof; and wherein the photosensitizing agent is selected from the group consisting of a porphyrin, phthalocyanine and a chlorin.

9. The method of claim 8, wherein the antigenic peptide is a vaccine antigen or vaccine component.

10. The method of claim 8, wherein the photosensitizing agent is meso-tetraphenylporphine with 4 sulfonate groups ($TPPS_4$), meso-tetraphenylporphine with 2 sulfonate groups on adjacent phenyl rings ($TPPS_{2a}$), or aluminum phthalocyanine with 2 sulfonate groups on adjacent phenyl rings ($AlPcS_{2a}$).

11. The method of claim 8, wherein the antigenic peptide and/or photosensitizing agent is bound to one or more targeting agents or carrier molecules.

12. The method of claim 8, wherein at least 90% of the cells are not killed.

13. The method of claim 8, wherein at least 95% of the cells are not killed.

14. The method of claim 8, wherein the photosensitizing agent is a sulfonated tetraphenylporphine, a disulfonated aluminum phthalocyanine or a tetrasulfonated aluminum phthalocyanine.

* * * * *

UNITED STATES PATENT AND TRADEMARK OFFICE
CERTIFICATE OF CORRECTION

| | | |
|---|---|---|
| PATENT NO. | : 8,216,587 B1 | Page 1 of 4 |
| APPLICATION NO. | : 09/524454 | |
| DATED | : July 10, 2012 | |
| INVENTOR(S) | : Berg et al. | |

It is certified that error appears in the above-identified patent and that said Letters Patent is hereby corrected as shown below:

On the Title page, in column 1, under "Inventors (75)", line 2, delete "H øgset and insert --Hogset--, therefor On the Title page, in column 1, under "Other Publications", line 1, delete "al." and insert --al.,--, therefor On the Title page, in column 1, under "Other Publications", line 1, delete "Photochem, and Photobio." and insert --"Photochem. and Photobio."--, therefor On the Title page, in column 1, under "Other Publications", line 2, delete "al" and insert --al.,--, therefor On the Title page, in column 1, under "Other Publications", line 2, delete "J. Photochem, and Photobio. B" and insert --"J. Photochem. and Photobio. B."--, therefor On the Title page, in column 1, under "Other Publications", line 3, delete "al" and insert --al.--, therefor On the Title page, in column 1, under "Other Publications", line 3, delete "Basic & Chemical Immunol." and insert --"Basic & Chemical Immunol.,"--, therefor On the Title page, in column 1, under "Other Publications", line 4, delete "al" and insert --al.--, therefor On the Title page, in column 1, under "Other Publications", line 4, delete "ImmunoBiology," and insert --"Immuno Biology,"--, therefor On the Title page, in column 1, under "Other Publications", line 9, delete "W.J.," and insert --W. J.--, therefor Signed and Sealed this
Twenty-sixth Day of March, 2013

Teresa Stanek Rea
*Acting Director of the United States Patent and Trademark Office*

CERTIFICATE OF CORRECTION (continued)
U.S. Pat. No. 8,216,587 B1

On the Title page, in column 2, under "Other Publications", line 7, delete "Thomas.J. ,et al. ," and insert --Thomas. J., et al.,--, therefor On the Title page, in column 2, under "Other Publications", line 8, delete "12,(Jan." and insert --12, (Jan.--, therefor On the Title page, in column 2, under "Other Publications", line 10, delete "Ronald.N. ," and insert --Ronald. N.,--, therefor On the Title page, in column 2, under "Other Publications", line 12, delete "Section,(Jan." and insert --Section, (Jan.--, therefor On the Title page, in column 2, under "Other Publications", line 13, delete "1994),287-299" and insert --1994), 287-299--, therefor On the Title page, in column 2, under "Other Publications", line 14, delete "Douglas.J. ,et al. ," and insert --Douglas. J., et al.,--, therefor On the Title page, in column 2, under "Other Publications", line 17, delete ",(Jan." and insert --, (Jan.--, therefor On the Title page, in column 2, under "Other Publications", line 18, delete "1998),70-75" and insert --1998), 70-75--, therefor On the Title page, in column 2, under "Other Publications", line 19, delete "Alexei.F. ,et al. ," and insert --Alexei. F., et al.,--, therefor On the Title page, in column 2, under "Other Publications", line 23, delete "1999,239-246" and insert --1999, 239-246--, therefor On the Title page, in column 2, under "Other Publications", line 24, delete "Kenneth.L. ,et al. ," and insert --Kenneth. L., et al.,--, therefor On the Title page, in column 2, under "Other Publications", line 26, delete "17,(Mar. 1996), 131-137" and insert --17, (Mar. 1996), 131-137--, therefor On the Title page, in column 2, under "Other Publications", line 27, delete "G..,et al. ," and insert --G. et al.,--, therefor On the Title page, in column 2, under "Other Publications", line 30, delete "8,(Oct." and insert --8, (Oct.--, therefor On the Title page, in column 2, under "Other Publications", line 31, Delete "1997),1183-1187" and insert --1997), 1183-1187--, therefor

CERTIFICATE OF CORRECTION (continued)
U.S. Pat. No. 8,216,587 B1

On the Title page, in column 2, under "Other Publications", line 32, delete "Jennifer.M. ,et al. ," and insert --Jennifer. M., et al.,--, therefor On the Title page, in column 2, under "Other Publications", line 35, delete "8,(Oct. 20, 1997),1213-1221" and insert --8, (Oct. 20, 1997), 1213-1221--, therefor On the Title page, in column 2, under "Other Publications", line 36, delete "Jonathan.W. ,et al. ," and insert --Jonathan. W., et al.,--, therefor On the Title page, in column 2, under "Other Publications", line 40, delete "52,(1992),1123" and insert --52, (1992), 1123--, therefor On the Title page, in column 2, under "Other Publications", line 41, delete "F ," and insert --F.,--, therefor On the Title page, in column 2, under "Other Publications", line 42, delete "H2O2" and insert --$H_2O_2$--, therefor On the Title page, in column 2, under "Other Publications", line 43, delete "2001),549-55" and insert --2001), 549-55--, therefor On the Title page, in column 2, under "Other Publications", line 44, delete "A ," and insert --A.,--, therefor On the Title page, in column 2, under "Other Publications", line 46, delete "1982 ,47-61" and insert --1982, 47-61--, therefor On page 2, in column 1, under "Other Publications", line 1, delete "B ," and insert --B.,--, therefor On page 2, in column 1, under "Other Publications", line 2, delete "(Feb. 1986),334-42" and insert --(Feb. 1986), 334-42--, therefor On page 2, in column 1, under "Other Publications", line 3, delete "J" and insert --J.--, therefor On page 2, in column 1, under "Other Publications", line 5, delete "(Jan. 1990),67-76" and insert --(Jan. 1990), 67-76--, therefor On page 2, in column 1, under "Other Publications", line 8, after "Pages", insert --,--, therefor On page 2, in column 1, under "Other Publications", line 13, delete "K. ," and insert --K.,--, therefor On page 2, in column 1, under "Other Publications", line 14-15, delete "(May 2005),133-47" and insert --(May. 2005), 133-47--, therefor

CERTIFICATE OF CORRECTION (continued)
U.S. Pat. No. 8,216,587 B1

On page 2, in column 1, under "Other Publications", line 16, delete "A. ," and insert --A.,--, therefor On page 2, in column 1, under "Other Publications", line 18, delete "(2006),521-36" and insert --(2006), 521-36--, therefor On page 2, in column 1, under "Other Publications", line 21, delete "(1996),4749-4757" and insert --(1996), 4749-4757--, therefor On page 2, in column 1, under "Other Publications", line 22, delete "D. ," and insert --D.,--, therefor On page 2, in column 1, under "Other Publications", line 24-25, delete "(1998),1750-1758" and insert --(1998), 1750-1758--, therefor On page 2, in column 2, under "Other Publications", line 3, delete "(1999),1180-1183" and insert --(1999), 1180-1183--, therefor On page 2, in column 2, under "Other Publications", line 6, delete "(2007),362-372" and insert --(2007), 362-372--, therefor On page 2, in column 2, under "Other Publications", line 9, delete "(1993),5920-5928" and insert --(1993), 5920-5928--, therefor On page 2, in column 2, under "Other Publications", line 15, delete "Biochimlca" and insert --Biochimica--, therefor On page 2, in column 2, under "Other Publications", line 16, delete "(2000),307-313" and insert --(2000), 307-313--, therefor On page 2, in column 2, under "Other Publications", line 19, delete "(2006),1451-1456" and insert --(2006), 1451-1456--, therefor On page 2, in column 2, under "Other Publications", line 23, after "Wilson, C. C., et al., "HIV-1-Specific CTL Responses Primed In Vitro by Blood-Derived Dendritic Cells and Th-1-Biasing Cytokines", The Journal of Immunology, 162, (1999), 3070-3078", insert
--Janeway, C., et al., "ImmunoBiology," 1994. Current Biology Ltd. Philadelphia, PA; pages 7.1-7.5.
--Janeway et al., "Immunobiology," 1994; Garland Publishing, New York. Pages 1:16-1:18.--, therefor

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: MART-1 peptide

<400> SEQUENCE: 1

Thr Ala Glu Glu Ala Ala Gly Ile Gly Ile Leu Thr Val Ile Leu Gly
1               5                   10                  15
```